United States Patent [19]

Schmolka

[11] 4,450,091

[45] May 22, 1984

[54] HIGH FOAMING LIQUID SHAMPOO COMPOSITION

[75] Inventor: Irving R. Schmolka, Grosse Ile, Mich.

[73] Assignee: BASF Wyandotte Corporation, Wyandotte, Mich.

[21] Appl. No.: 480,756

[22] Filed: Mar. 31, 1983

[51] Int. Cl.$^3$ .................. A61K 7/06; C11D 17/00; C11D 1/83

[52] U.S. Cl. ..................... 252/174.21; 252/173; 252/174.22; 252/DIG. 1; 252/DIG. 14; 252/DIG. 2; 252/DIG. 7; 252/DIG. 13; 424/70

[58] Field of Search ............ 252/174.21, 174.22, 252/173, DIG. 1, DIG. 2, DIG. 7, DIG. 13, DIG. 14; 424/70

[56] References Cited

U.S. PATENT DOCUMENTS

| | | | |
|---|---|---|---|
| 2,828,345 | 3/1958 | Spriggs | 252/DIG. 1 X |
| 3,101,374 | 8/1963 | Patton | 252/174.21 X |
| 3,337,463 | 8/1967 | Schmolka | 252/529 X |
| 3,869,399 | 3/1975 | Collins | 252/117 X |
| 3,925,241 | 12/1975 | Schmolka | 252/106 X |
| 4,247,425 | 1/1981 | Egan et al. | 252/548 X |
| 4,256,611 | 3/1981 | Egan et al. | 252/548 X |
| 4,326,977 | 4/1982 | Schmolka | 252/173 X |
| 4,343,726 | 10/1982 | Egan et al. | 252/547 |

FOREIGN PATENT DOCUMENTS

722746 1/1955 United Kingdom .

*Primary Examiner*—John E. Kittle
*Assistant Examiner*—Mukund J. Shah
*Attorney, Agent, or Firm*—Bernhard R. Swick

[57] ABSTRACT

It has been found in accordance with the instant invention that the viscosity of a shampoo formulation based on a blend of amphoteric and nonionic surfactants could be considerably enhanced by replacement of a part of the amphoteric surfactant with an anionic surfactant. The shampoo compositions also contain as essential ingredients both an alkanolamide and a polyoxyalkylene glycol fatty ester. These shampoo products are characterized by increased viscosity as well as mildness towards the eyes and superior foam compared to some leading commercial products.

The nonionic surfactant is a cogeneric mixture of conjugated polyoxybutylene-polyoxyethylene compounds containing in their structure oxybutylene groups, oxyethylene groups and an organic radical derived from an organic compound containing a pluarlity of reactive hydrogen atoms.

11 Claims, No Drawings

HIGH FOAMING LIQUID SHAMPOO COMPOSITION

BACKGROUND OF THE INVENTION

1. Field of the Invention

This invention relates to shampoo compositions containing nonionic, amphoteric and anionic surfactants characterized by unexpectedly high viscosity.

2. Description of the Prior Art

The preparation of shampoo products is an old established art. A satisfactory shampoo must lather well in the presence of the natural sebum soil found in the hair and should not irritate the eyes. In recent years there has been a trend away from the use of harsh, high-foaming anionic surfactants, such as salts of lauryl sulfate and lauryl ether sulfate towards the use of amphoterics or nonionics or blends thereof. This results in products which are less irritating to the eyes. However, the use of these types of surfactants can result in shampoo products which are very fluid, rather than the viscous products the consumer prefers.

REFERENCES OF INTEREST

U.S. Pat. No. 4,326,977 discloses a skin cleansing composition comprising an antiseptic agent, a polyoxyethylene-polyoxybutylene block copolymer and water.

U.S. Pat. No. 3,869,399 discloses a detergent composition containing a mixture of a nonionic surfactant, an anionic surfactant and ethanolamine. One of the nonionic surfactants suggested is the condensation product of ethylene oxide with a hydrophobic base formed by the condensation of propylene oxide with propylene glycol.

U.S. Pat. No. 3,925,241 discloses amphoteric surfactant gels useful as hair shampoos, etc., prepared from polyoxypropylene-polyoxyethylene block copolymers as gelling agents.

U.S. Pat. No. 2,828,345 discloses hydroxypolyoxyethylene diethers of polyoxybutylene glycols which are useful for dispersing solids such as pigments and in liquids as thickening agents.

U.S. Pat. No. 3,101,374 and British Pat. No. 722,746 disclose butylene oxide-ethylene oxide nonionic surfactants and indicate that they have good detergent properties.

U.S. Pat. No. 4,256,611 and U.S. Pat. No. 4,247,425 disclose aqueous household cleaning compositions and shampoos which consist essentially of a combination of a nonionic surfactant in the form of an ethylene oxide adduct of partial glycerol esters of detergent grade fatty acid and an anionic surfactant which combination optionally includes a foam stabilizing amount of an alkanolamide or a tertiary amine oxide. These compositions have the ability to vary extensively the viscosity of dilute aqueous solutions thereof through the appropriate choice of the nonionic surfactant component.

U.S. Pat. No. 3,337,463 relates to nonionic detergent compositions having enhanced and stabilized foaming characteristics which consist essentially of a mixture of polyoxyalkylene condensates of cellulose and at least one nonionic surfactant such as a mixture of conjugated polyoxyethylene-polyoxypropylene compounds.

The BASF Wyandotte "cosmetic formulary" includes therein various shampoo compositions using polyoxyethylene-polyoxypropylene block copolymer nonionic surfactants.

SUMMARY OF THE INVENTION

It has been found in accordance with the instant invention that the viscosity of a shampoo formulation based on a blend of amphoteric and nonionic surfactants could be considerably enhanced by replacement of a part of the amphoteric surfactant with an anionic surfactant. The shampoo compositions also contain as essential ingredients both an alkanolamide and a polyoxyalkylene glycol fatty ester. These shampoo products are characterized by increased viscosity as well as mildness towards the eyes and superior foam compared to some leading commercial products.

A preferred embodiment of the invention relates to a shampoo comprising by weight from about 2 to 25 percent nonionic surfactant, from about 1 to 5 percent anionic surfactant, about 4 to 20 percent amphoteric surfactant, about 1 to 5 percent alkanolamide, about 1 to 5 percent polyoxyalkylene glycol fatty ester and about 40 to 85 percent water. In a most preferred embodiment, the shampoo composition comprises by weight about 6 to 15 percent nonionic surfactant, about 1 to 3 percent anionic surfactant, about 6 to 15 percent amphoteric surfactant, about 1 to 3 percent alkanolamide, about 1 to 3 percent polyoxyalkylene glycol fatty ester and about 50 to 65 percent water.

The nonionic surfactant is a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom, thereby principally constituting a polyoxybutylene polymer. The oxyethylene groups are attached to the polyoxybutylene polymer in polyoxyethylene chains. The average molecular weight of the polyoxybutylene polymers in the mixture is at least about 500, as determined by hydroxyl number, and the oxyethylene groups present constitute 65 to 80 percent by weight of the compound.

DESCRIPTION OF THE PREFERRED EMBODIMENTS

The nonionic surfactant of use in the invention is a cogeneric mixture of conjugated polyoxybutylene polyoxyethylene compounds having as a hydrophobe, a polyoxybutylene polymer of at least 500 molecular weight. The polyoxybutylene compounds are prepared by first condensing butylene oxide with an organic compound containing a plurality of reactive hydrogen atoms to prepare a polyoxybutylene polymer of at least 500 molecular weight, and subsequently condensing ethylene oxide therewith. The compounds used in this invention conform to the following generic formula:

$$Y[(C_4H_8O)_n\text{-}E\text{-}H]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 500, as determined by hydroxyl number; E is a polyoxyalkylene chain wherein the oxygen/carbon atom ratio is at least 0.5, and E constitutes 65 percent by weight to 80 percent by weight of the compound.

The polyoxybutylene polymer, which is an intermediate in the preparation of the compounds of use in this invention, has the following structure:

$$Y[(C_4H_8O)_nH]_x \quad (B)$$

wherein Y, n and x are defined as in Formula A above.

The preferred compounds of use in this invention are prepared by condensing ethylene oxide in an amount between 65 and 80 percent by weight of the resultant compound, with the polyoxybutylene polymer. These compounds have the following formula $$Y[(C_4H_8O)_n(C_2H_4O)_mH]_x \quad (C)$$

wherein Y, n and x are defined as in Formula A and m has a value such that the oxyethylene groups constitute 65 to 80 percent by weight of the compound.

When ethylene oxide is condensed with a polyoxybutylene glycol of at least 500 molecular weight and derived from a butanediol initiator, the resulting compounds have the following structure:

$$HO(C_2H_4O)_m(C_4H_8O)_n(C_2H_4O)_{m'}H \quad (D)$$

where n is defined as previously set forth; and $m'+m$ have a value such that the oxyethylene groups constitute 65 percent by weight to 80 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators which may include water, diols such as propane diol, butanediol, triols such as glycerol and trimethylol propane, tetrols such as pentaerythritol as well as initiators containing more than four hydroxyl groups such as hexitol or sucrose. Also, amines and other low molecular weight water-soluble compounds having two or more active hydrogen atoms, such as ethylene diamine or diethylene triamine, may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the surfactants used in this invention. In lieu of butylene oxide, other 4-carbon cyclic ethers such as methyloxetane, tetrahydrofuran and isobutylene oxide may be used.

Surfactants of the invention, conforming to structure D above, are those surfactants which contain a hydrophobe of between about 600 and about 1800 molecular weight and an ethylene oxide content of from about 65 to 80 percent by weight of the surfactant. Preferably used is a surfactant having a hydrophobe of about 1200 molecular weight and containing about 70 percent by weight ethylene oxide. The nonionic surfactant is used in an amount between 2 and 25 percent by weight of the shampoo.

Examples of amphoteric surfactants useful in the invention are generally water soluble salts of derivatives of aliphatic amines which contain at least one cationic group, ergo, non-quaternary nitrogen, quaternary ammonium, or quaternary phosphonium group, at least one alkyl group of about 8 to 18 carbon atoms and an anionic water solubilizing carboxyl, sulfo, sulfato, phosphato or phosphono group in their molecular structure. Cocoamidopropyl betaine is useful. The alkyl group may be straight chain or branched and the specific cationic atom may be part of a heterocyclic ring. Specific examples are disclosed in U.S. Pat. Nos. 3,849,548, 3,959,462, and 4,061,602.

Suitable anionic surfactants include those surface-active agents which contain an organic hydrophobic group containing generally 8 to 26 carbon atoms, preferably 10 to 18 carbon atoms in their molecular structure, and at least one water solubilizing group selected from the group of sulfonate, sulfate, carboxylate, phosphonate and phosphate so as to form a water-soluble detergent. Specific examples of suitable anionic surfactants are disclosed in U.S. Pat. Nos. 3,849,548, 4,126,674, 4,061,602, and 3,928,251.

Other nonionic surfactants such as ethoxylated sorbitan esters may be used. Cationic surfactants may also be included such as those disclosed in U.S. Pat. Nos. 3,849,548, 3,959,462 and 4,126,624. The cationic surfactants may be used in an amount between about 0.2 to 5.0 percent by weight.

An essential component of the instant composition for achieving high viscosity is an alkanolamide. Suitable alkanolamides include lauramide, lauramide MEA, lauramide MIPA, lauramidopropylamine oxide, lauramidopropyl dimethylamine, lauramide DEA, myristamide DEA, oleamide DEA, palmitamide DEA and behenamidopropyl dimethylamine, all as described in the CTFA Cosmetic Ingredient Distionary, Third Edition, published by The Cosmetic, Toiletry and Fragrance Association, Inc., Washington, D.C.

Another essential component for achieving high viscosity is a polyoxyalkylene glycol fatty ester. Particularly useful for this purpose is polyoxyethylene glycol 6000 distearate. Other useful polyoxyalkylene glycol fatty esters are polyoxyethylene glycol 4000 distearate, polyethylene glycol 6000 ditallowate, polyethylene glycol 4000 dieicosate, polyethylene glycol 8000 distearate, polyethylene glycol 6000 dipalmitate, polyethylene glycol 8000 monostearate and polyethylene glycol 20,000 monostearate.

The shampoo compositions of certain embodiments of this invention may also include additives such as foam boosting and foam stabilizing agents, for example amine oxides such as lauryl dimethyl amine oxide and those additives such as disclosed in U.S. Pat. No. 3,769,398, such as 1-hydroxy-ethyl-2-Cocoimidazoline and 2-Coco, 4,4-dihydroxy methyloxazoline. Other suitable additives for the shampoo compositions of this invention include calcium and magnesium ion-chelating agents, such as ethylenediaminetetra-acetic acid (EDTA) and other sequestering agents; inorganic or organic acids, such as phosphoric and citric acid; or alkalis, to adjust pH; preservatives such as methyl p- hydroxybenzoate and other anti-microbial agents; perfume, lanolin and its derivatives or other emollients, conditioning agents, water and anti-dandruff agents, dyes, alcohol, glycol, other thickening agents such as cellulose derivatives, gums, and opacifiers. The additives are added in an amount between about 1 and 35, preferably 5 and 15 percent by weight of the shampoo. Each additive, if included, is used in an amount between 0.01 and 8.0 percent by weight. It is understood that not all of the abovementioned additives will be used in each shampoo formulation. The expert in shampoo formulation is able to adjust the type and quantity of additives necessary to arrive at a suitable shampoo formulation.

The shampoos of the invention are prepared as follows: water is added to a vessel equipped with a mechanical stirrer. The other ingredients are added slowly, individually or as a group, and mixed until dissolved. Some heat may be used to hasten solution. The perfume and preservative are added last after a homogeneous solution is formed.

The following examples will further illustrate the various aspects of the invention. Where not otherwise specified throughout this specification and claims, temperatures are in degrees Centigrade, and parts, percentages and proportions are by weight.

EXAMPLES 1-7

Examples 1, 2, 6 and 7 are examples of shampoo formulations of the invention, and Examples 3-5 are comparison examples all prepared according to the preceding description. The compositions are set forth in Table I below.

TABLE I

| Component | Example No. (Parts by Weight) | | | | | | |
|---|---|---|---|---|---|---|---|
| | 1 | 2 | 3 | 4 | 5 | 6 | 7 |
| Nonionic | 11.6 | 11.6 | 11.6 | 11.6 | 11.6 | 11.6 | 11.6 |
| Sodium lauryl ether sulfate | 3.5 | — | — | 3.5 | 3.5 | — | — |
| Tetrahydroxy propyl ethylene diamine lauryl ether sulfate (53.5% active) | — | — | — | — | — | 3.8 | — |
| Triethanolamine lauryl Ether Sulfate | — | 5.9 | — | — | — | — | — |
| Cocamidopropyl betaine (30% active) | 21.3 | 21.3 | 28.0 | 21.3 | 21.3 | 21.3 | 21.3 |
| Lauric diethanolamide | 3.0 | 3.0 | 3.0 | — | 3.0 | 3.0 | 3.0 |
| PEG 6000 distearate | 2.0 | 2.0 | 2.0 | 2.0 | — | 2.0 | 2.0 |
| 99.8% citric acid | 0.1 | 0.1 | 0.1 | 0.1 | 0.1 | 0.1 | 0.1 |
| Distilled water | 58.5 | 56.1 | 55.3 | 61.5 | 60.5 | 58.2 | 56.9 |
| α-olefin sulfonate | | | | | | | 5.1 |

The nonionic of Table I is a polyoxybutylene-polyoxyethylene nonionic surfactant made from a polyoxybutylene hydrophobe prepared from condensing 1,2-butylene oxide with a 1,4-butanediol initiator having an approximate average molecular weight of the polyoxybutylene hydrophobe of about 1200 and a polyoxyethylene hydrophile content of about 80 percent by weight of the surfactant.

In order to show the surprisingly high viscosity values of a shampoo of this invention, (Examples 1, 2, 6 and 7) when compared with shampoos that do not include all five essential components (Examples 3-5) and with three commercial shampoos of the prior art, viscosity tests were run on the shampoos of Examples 1-7 and comparisons M, N and O which are commercial shampoos. These values are shown in Table II below.

Also Bacon foam height tests were conducted on applicant's compositions and the comparative compositions. The foam heights of a 15 percent solution, as is, and the foam heights of a 15 percent solution with 1 percent synthetic sebum soil are shown in Table II.

TABLE II

| Formulation | Viscosity, cps | Bacon Foam, ml | |
|---|---|---|---|
| | | No Soil | + 1% Soil |
| 1 | 14,000 | 700/700 | 250/250 |
| 2 | 12,250 | 370/370 | 340/340 |
| 3 | 2490 | 730/730 | 190/180 |
| 4 | 230 | 380/380 | 260/260 |
| 5 | 600 | 650/650 | 280/280 |
| 6 | 6,400 | 650/630 | 200/190 |
| 7 | 22,550 | 700/700 | 330/330 |
| M | 5,340 | 240/100 | 100/100 |
| N | 570 | 200/100 | 140/100 |
| O | 3,855 | 130/110 | 100/100 |

EXAMPLE 8

Example 1 is repeated with the exception that the nonionic of Example 1 is replaced with a polyoxybutylene-polyoxyethylene nonionic surfactant having an approximate average molecular weight of the polyoxybutylene hydrophobe of about 700, and a polyoxyethylene hydrophile content of about 65 percent by weight of the surfactant. The shampoo composition is characterized by unexpectedly high viscosity and high foaming characteristics.

EXAMPLE 9

Example 1 is repeated with the exception that the nonionic of Example 1 is replaced with a polyoxybutylene-polyoxyethylene nonionic surfactant having an approximate average molecular weight of the polyoxybutylene hydrophobe of about 2500, and a polyoxyethylene hydrophile content of about 65 percent by weight of the surfactant. The shampoo composition is characterized by unexpectedly high viscosity and high foaming characteristics.

The embodiments of the invention in which an exclusive privilege or property is claimed are defined as follows:

1. A liquid shampoo having a viscosity greater than about 6400 centipoise comprising by weight about 2 to 25 percent nonionic surfactant, about 1 to 5 percent anionic surfactant, about 4 to 20 percent amphoteric surfactant, about 1 to 5 percent alkanolamide, about 1 to 5 percent polyoxyalkylene glycol di fatty acid ester and about 40 to 85 percent by weight water, said nonionic surfactant being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 500, as determined by hydroxyl number, and the oxyethylene groups present constituting 65 to 80 percent, by weight, of the mixture.

2. The shampoo of claim 1 wherein the polyoxybutylene polymer molecular weight is about 700 to 2500.

3. The shampoo of claim 1, wherein the liquid shampoo additionally comprises 0 to 50 percent by weight of other surfactants and 1 to 35 percent by weight of additives.

4. The shampoo of claim 3 wherein the polyoxybutylene polymer molecular weight is about 600 to 1800.

5. The shampoo of claim 3 wherein the amphoteric surfactant is selected from the group consisting of water-soluble salts of derivatives of aliphatic amines containing at least one cationic group, at least one alkyl group of about 8 to 18 carbon atoms and an anionic water-solubilizing carboxyl, sulfo, sulfato, phosfato or phosphono group in its molecular structure.

6. The shampoo of claim 5 wherein the polyoxybutylene polymer molecular weight is about 600 to 1800.

7. The shampoo of claim 3, wherein said anionic surfactant is selected from the group consisting of surface active agents containing an organic hydrophobic group having about 8 to 26 carbon atoms in their molecular structure and at least one water-solubilizing group selected from the group consisting of sulfonates, sulfates, carboxylates, phosphonate and phosphate groups.

8. The shampoo of claim 7 wherein the polyoxybutylene polymer molecular weight is about 600 to 1800.

9. The shampoo of claim 7 wherein the amphoteric surfactant is selected from the group consisting of water-soluble salts of derivatives of aliphtic amines containing at least one cationic group, at least one alkyl group of about 8 to 18 carbon aoms and an anionic water-solubilizing carboxyl, sulfo, sulfato, phosfato or phosphono group in its molecular structure.

10. The shampoo of claim 9 wherein the polyoxybutylene polymer molecular weight is about 600 to 1800.

11. The shampoo of claim 1 wherein the polyoxyalkylene glycol fatty ester is a diester.

* * * * *